United States Patent
Hoff et al.

(10) Patent No.: US 6,315,730 B1
(45) Date of Patent: Nov. 13, 2001

(54) ULTRASOUND IMAGING OF TISSUE PERFUSION BY PULSE ENERGY DISRUPTION OF CONTRAST AGENT

(75) Inventors: Lars Hoff; Jonny Østensen, both of Oslo; Sigmund Frigstad, Trondheim; Morten Eriksen, Oslo, all of (NO)

(73) Assignee: Nyomed Imaging AS, Oslo (NO)

( * ) Notice: Subject to any disclaimer, the term of this patent is extended or adjusted under 35 U.S.C. 154(b) by 0 days.

(21) Appl. No.: 09/425,290

(22) Filed: Oct. 25, 1999

Related U.S. Application Data

(63) Continuation of application No. PCT/GB98/01217, filed on Apr. 24, 1998.
(60) Provisional application No. 60/044,408, filed on Apr. 29, 1997.

(30) Foreign Application Priority Data

Apr. 24, 1997 (GB) .................................... 9708246

(51) Int. Cl.[7] ....................................................... A61B 8/14
(52) U.S. Cl. .............................................................. 600/458
(58) Field of Search .................................... 600/437, 440, 600/441, 443, 454, 458; 424/9, 9.5, 450, 9.52; 73/602; 364/413.25

(56) References Cited

U.S. PATENT DOCUMENTS

| | | |
|---|---|---|
| 5,040,537 | 8/1991 | Katakura . |
| 5,235,984 * | 8/1993 | D'Sa ................................. 600/443 |
| 5,456,257 * | 10/1995 | Johnson et al. ..................... 600/458 |
| 5,556,610 * | 9/1996 | Yan et al. ........................... 424/9.52 |
| 5,560,364 * | 10/1996 | Porter ................................. 600/458 |
| 5,601,086 * | 2/1997 | Pretlow, III et al. ................ 600/458 |
| 5,678,553 | 10/1997 | Uhlendorf et al. . |
| 5,735,281 | 4/1998 | Rafter et al. . |
| 5,833,613 * | 11/1998 | Averkiou et al. ................... 600/440 |

FOREIGN PATENT DOCUMENTS

| | | |
|---|---|---|
| 0 713 680 A | 5/1996 | (EP) . |
| 0 713 680 A2 | 5/1996 | (EP) . |
| 0 770 352 A | 5/1997 | (EP) . |
| 0 770 352 A1 | 5/1997 | (EP) . |
| WO 98 05364 A | 2/1998 | (WO) . |
| WO 98/05364 | 2/1998 | (WO) . |
| WO 98/10798 | 3/1998 | (WO) . |
| WO 98/10798 A | 3/1998 | (WO) . |
| WO 98 17324 A | 4/1998 | (WO) . |
| WO 98/17324 | 4/1998 | (WO) . |
| WO 98 18501 A | 5/1998 | (WO) . |
| WO 98/18501 | 5/1998 | (WO) . |

OTHER PUBLICATIONS

Abstract XP–002077429: *J. Am. Coll. Cardiol.*, Feb. 1, 1997 (publ. Mar. 16, 1997) K. Wei et al.
Basic Science Reports, Quantification of Myocardial Blood Flow with Ultrasound–Induced Destruction of Microbubbles Administered as a Constant Venous Infusion, Wei et al., pp. 473–483, 1998.

* cited by examiner

*Primary Examiner*—Brian L. Casler
*Assistant Examiner*—Ali M. Imam
(74) *Attorney, Agent, or Firm*—Royal N. Ronning, Jr.

(57) ABSTRACT

A method of measuring tissue perfusion in a human or non-human animal subject which comprises administering an effective amount of an ultrasound contrast agent to said subject, irradiating tissue in a target region with at least one pulse of ultrasound having energy sufficient to destroy or discernibly modify the echogenic properties of substantially all contrast agent in said target region, and ultrasonically detecting and quantifying the rate of flow of either further contrast agent into said target region or modified contrast agent out of said target region.

11 Claims, 2 Drawing Sheets

ULTRASOUND IMAGING OF TISSUE PERFUSION BY PULSE ENERGY DISRUPTION OF CONTRAST AGENT

This application is a continuation of pending international application number PCT/GB98/01217 filed Apr. 24, 1998 (of which the entire disclosure of the pending, prior application is hereby incorporated by reference), which itself is a continuation-in-part of U.S. provisional application No. 60/044,408 filed Apr. 29, 1997.

This invention relates to ultrasound imaging, more particularly to the use of ultrasound imaging in measuring tissue perfusion.

It is well known that contrast agents comprising dispersions of gas microbubbles are particularly efficient backscatterers of ultrasound by virtue of the low density and ease of compressibility of the microbubbles. Such microbubble dispersions, if appropriately stabilised, may permit highly effective ultrasound visualisation of, for example, the vascular system and tissue microvasculature, often at advantageously low doses.

Measurements of tissue perfusion are of importance in, for example, tumour detection, tumour tissue typically having different vascularity from healthy tissue, and studies of the myocardium, e.g. to evaluate the blood supply thereto. Whilst contrast agent detection using current ultrasound imaging techniques may provide information as to whether particular organs or regions thereof are perfused or not, it does not readily permit quantification of levels of perfusion. Such information, which is useful in assessing whether a patient is at risk owing to low perfusion and so may benefit from preventative methods and/or treatment, must currently be obtained using radioisotopic imaging techniques such as scintigraphy, positron emission tomography or single photon emission computed tomography. These techniques all involve injection of radioactive substances, with potential safety risks for both the patient and medical staff, and use of expensive imaging equipment; this inevitably prohibits their widespread use.

The present invention is based on the finding that ultrasound imaging involving ultrasound-induced destruction or modification of contrast agents may be used to give a measure of tissue perfusion, thereby permitting ready and inexpensive measurement of relative rates of tissue perfusion in any tissue susceptible to ultrasound imaging.

There is currently a limited body of prior art pertaining to ultrasound imaging involving contrast agent destruction. It is stated in U.S. Pat. No. 5425366 that certain types of microparticulate ultrasound contrast agents, for example gas-containing polymer microcapsules, may be visualised by colour Doppler techniques despite being essentially motionless, e.g. as a result of uptake by the reticuloendothelial system. It is proposed that the relatively high irradiation energy levels associated with colour Doppler investigations cause the microparticles to burst, thereby generating Doppler-sensitive signals described as "acoustically stimulated acoustic emission", although it seems more likely that in practice the detector interprets the discontinuity in the backscattered signal as a motion event and generates an appropriate display. It will be appreciated that since this technique is concerned exclusively with detection of essentially motionless contrast agent microparticles it is inherently inapplicable to measurement of rates of perfusion.

U.S. Pat. No. 5456257 describes detection of coated microbubble contrast agents in the bodies of patients by applying pulses of ultrasound irradiation at energy levels sufficient to destroy the coated microbubbles and identifying microbubble destruction events using phase insensitive detection (e.g. envelope detection) and differentiation of echoes received from successive ultrasound transmissions. Following the first transmission, acoustic energy emanating from microbubble destruction sites is received by an ultrasonic transducer and the resulting signal waveform is subject to amplitude detection; echoes received from a subsequent transmission are detected in similar manner and signals from the two reception periods are differentiated on a spatial basis. Typically the signals derived from the second reception period are subtracted from those derived from the first reception period to generate signals emanating from microbubble destruction events to the exclusion of other signals; thresholding may be applied to eliminate variations arising from tissue movements and flowing fluids. Whilst signals may be processed using sustain Systems and/or by counting events in a given region of the body over a period of time, thereby giving an indication of bulk flow of contrast agent-containing blood in, for example, the chambers of the heart, there is no suggestion that the technique may be used in quantifying capillary blood flow within tissue, i.e. of measuring perfusion.

The present invention similarly uses a first high energy ultrasound pulse or series of pulses to destroy or discernibly modify a recognisable amount of the contrast agent within a target region, but rather than employing subsequent pulses to detect background signals to be subtracted from the first detection sequence the invention uses the subsequent pulses to detect the flow of "fresh" or unmodified contrast agent (and therefore blood) into the target region. This permits determination of parameters such as vascular blood volume fraction, mean transit time and tissue perfusion with respect to local vascular state within the target region. The initial high energy pulse or pulses may, for example, be used to clear a closely defined target region of detectable contrast agent so that a sharp front of further contrast agent, which is readily detectable and quantifiable by ultrasound imaging, then flows into this region. The ability to generate sharp fronts of moving contrast agents in target regions of interest renders the method of substantial advantage over previous attempts to estimate wash-in rates of contrast agents into tissue immediately following injection, since the front of injected contrast agent will inevitably be smoothed or smeared out by passage through the lungs and heart. Alternatively the initial pulse or pulses may be used to modify the echogenicity of the contrast agent, for example by activating a contrast agent in precursor form so as to produce a rise in echogenicity in the target region. The time course of echogenicity change during and after ultrasound exposure may give information about local vascular state, e.g. regional blood volume and perfusion. For example, the wash-out rate of contrast agent, having been activated by ultrasound exposure, may be determined and thus used to map perfusion.

Thus, according to one aspect of the present invention, there is provided a method of measuring tissue perfusion in a human or non-human animal subject which comprises administering an effective amount of an ultrasound contrast agent to said subject, irradiating tissue in a target region with at least one pulse of ultrasound having energy sufficient to destroy or discernibly modify the echogenic properties of a recognisable amount of the contrast agent in said target region, and ultrasonically detecting and quantifying the rate of flow of either further contrast agent into said target region or modified contrast agent out of said target region.

Viewed from another aspect the invention provides the use of an ultrasound contrast agent in the manufacture of a diagnostic material for use in a method of measuring tissue perfusion in a human or non-human animal subject, said method comprising administering an effective amount of said ultrasound contrast agent to said subject, irradiating tissue in a target region with at least one pulse of ultrasound having energy sufficient to destroy or discernibly modify the echogenic properties of a recognisable amount of the contrast agent in said target region, and ultrasonically detecting and quantifying the rate of flow of either further contrast agent into said target region or modified contrast agent out of said target region.

A wide range of ultrasound contrast agents may be employed in accordance with the method of the invention; most commonly these contrast agents will be gas-containing or gas-generating. Representative examples of such contrast agents include microbubbles of gas stabilised (e.g. at least partially encapsulated) by a coalescence-resistant surface membrane (for example gelatin, e.g. as described in WO-A-8002365), a filmogenic protein (for example an albumin such as human serum albumin, e.g. as described in U.S. Pat. No. 4718433, U.S. Pat. No. 4774958, U.S. Pat. No. 4844882, EP-A-0359246, WO-A-9112823, WO-A9205806, WO-A-9217213, WO-A-9406477 or WO-A-9501187), a polymer material (for example a synthetic biodegradable polymer as described in EP-A-0398935, an elastic interfacial synthetic polymer membrane as described in EP-A-0458745, a microparticulate biodegradable polyaldehyde as described in EP-A-0441468, a microparticulate N-dicarboxylic acid derivative of a polyamino acid - polycyclic imide as described in EP-A-0458079, or a biodegradable polymer as described in WO-A-9317718 or WO-A-9607434), a non-polymeric and nonpolymerisable wall-forming material (for example as described in WO-A-9521631), or a surfactant (for example a polyoxyethylene-polyoxypropylene block copolymer surfactant such as a Pluronic, a polymer surfactant as described in WO-A-9506518, or a film-forming surfactant such as a phospholipid, e.g. as described in WO-A-9211873, WO-A-9217212, WO-A-9222247, WO-A-9428780, WO-A-9503835, WO-A-9640275 or WO-A-9729783.

Other useful gas-containing contrast agents include gas-containing solid systems, for example microparticles (especially aggregates of microparticles) having gas contained therewithin or otherwise associated therewith (for example being adsorbed on the surface thereof and/or contained within voids, cavities or pores therein, e.g. as described in EP-A-0122624, EP-A-0123235, EP-A-0365467, WO-A-9221382, WO-A-9300930, WO-A-9313802, WO-A-9313808 or WO-A-9313809).

Multicomponent contrast agent formulations, for example comprising a dispersed gas phase-containing composition and a composition comprising a volatile component capable of transferring into said dispersed gas phase in vivo, e.g. by diffusion, may also be useful. Such contrast agents are described in the specification of our unpublished International Patent Application No. PCT/GB97/02898. They may if desired be prepared in precursor form such that the contrast agent only exhibits significant echogenicity following activation by high energy ultrasonication.

The disclosures of all of the above-described documents relating to gas-containing contrast agents are incorporated herein by reference.

Where phospholipid-containing compositions are employed in accordance with the invention, e.g. in the form of phospholipid-stabilised gas microbubbles, representative examples of useful phospholipids include lecithins (i.e. phosphatidylcholines), for example natural lecithins such as egg yolk lecithin or soya bean lecithin and synthetic or semisynthetic lecithins such as dimyristoylphosphatidylcholine, dipalmitoylphosphatidylcholine or distearoylphosphatidylcholine; phosphatidic acids; phosphatidylethanolamines; phosphatidylserines; phosphatidylglycerols; phosphatidylinositols; cardiolipins; sphingomyelins; fluorinated analogues of any of the foregoing; mixtures of any of the foregoing and mixtures with other lipids such as cholesterol. The use of phospholipids predominantly (e.g. at least 75%) comprising-molecules individually bearing net overall charge, e.g. negative charge, for example as in naturally occurring (e.g. soya bean or egg yolk derived), semisynthetic (e.g. partially or fully hydrogenated) and synthetic phosphatidylserines, phosphatidylglycerols, phosphatidylinositols, phosphatidic acids and/or cardiolipins, may be particularly advantageous.

Any biocompatible gas may be present in the microbubbles according to the invention, the term "gas" as used herein including any substances (including mixtures) substantially or completely in gaseous (including vapour) form at the normal human body temperature of 37° C. The gas may thus, for example, comprise air; nitrogen; oxygen; carbon dioxide; hydrogen; an inert gas such as helium, argon, xenon or krypton; a sulphur fluoride such as sulphur hexafluoride, disulphur decafluoride or trifluoromethylsulphur pentafluoride; selenium hexafluoride; an optionally halogenated silane such as methylsilane or dimethylsilane; a low molecular weight hydrocarbon (e.g. containing up to 7 carbon atoms), for example an alkane such as methane, ethane, a propane, a butane or a pentane, a cycloalkane such as cyclopropane, cyclobutane or cyclopentane, an alkene such as ethylene, propene, propadiene or a butene, or an alkyne such as acetylene or propyne; an ether such as dimethyl ether; a ketone; an ester; a halogenated low molecular weight hydrocarbon (e.g. containing up to 7 carbon atoms); or a mixture of any of the foregoing. Advantageously at least some of the halogen atoms in halogenated gases are fluorine atoms; thus biocompatible halogenated hydrocarbon gases may, for example, be selected from bromochlorodifluoromethane, chlorodifluoromethane, dichlorodifluoromethane, bromotrifluoromethane, chlorotrifluoromethane, chloropentafluoroethane, dichlorotetrafluoroethane, chlorotrifluoroethylene, fluoroethylene, ethylfluoride, 1,1-difluoroethane and perfluorocarbons, e.g. perfluoroalkanes such as perfluoromethane, perfluoroethane, perfluoropropanes, perfluorobutanes (e.g. perfluoro-n-butane, optionally in admixture with other isomers such as perfluoro-isobutane), perfluoropentanes, perfluorohexanes and perfluoroheptanes; perfluoroalkenes such as perfluoropropene, perfluorobutenes (e.g. perfluorobut-2-ene) and perfluorobutadiene; perfluoroalkanes such as perfluorobut-2-yne; and perfluorocycloalkanes such as perfluorocyclobutane, perfluoromethylcyclobutane, perfluorodimethylcyclobutanes, perfluorotrimethylcyclobutanes, perfluorocyclopentane, perfluoromethylcyclopentane, perfluorodimethylcyclopentanes, perfluorocyclohexane, perfluoromethylcyclohexane and perfluorocycloheptane. Other halogenated gases include methyl chloride, fluorinated (e.g. perfluorinated) ketones such as perfluoroacetone and fluorinated (e.g. perfluorinated) ethers such as perfluorodiethyl ether. The use of perfluorinated gases, for example sulphur hexafluoride and perfluorocarbons such as perfluoropropane, perfluorobutanes and perfluoropentanes, may be particularly advantageous in view of the recognised high stability in the bloodstream of microbubbles containing such gases.

The initial high energy ultrasound pulse or pulses may for example cause destruction of gas-containing contrast agents, e.g. by rupturing stabilising surface membranes such as proteins, polymers or film-forming surfactants, and/or by promoting dissolution of the gas content into surrounding tissue fluids. It will be appreciated, however, that it is not necessary wholly to destroy the echogenicity of the contrast agent in the target region, it being sufficient to modify its "acoustic signature" such that it may be distinguished ultrasonically from subsequently inflowing "fresh" contrast agent. Thus, for example, ultrasound-induced partial or complete disruption of encapsulating shell material may generate gas microbubbles which oscillate more freely than contrast agent-encapsulated gas and so exhibit discernibly modified acoustic properties. Alternatively the initial ultrasound irradiation may induce other echogenicity-modifying changes in parameters such as the composition, dimensions and/or mechanical properties of the contrast agent moieties; this may for example be used to lead to activation of a contrast agent in precursor form.

If desired, the contrast agent may be designed to be particularly sensitive to disruption by the initial ultrasound pulse(s), thereby limiting the intensity required for the initial ultrasound irradiation. This may, for example, be achieved by employing stabilising amphiphilic lipid material in the form of monolayers; the use of charged amphiphilic material, e.g. negatively charged phospholipids, may encourage the formation of monolayers as a result of electronic repulsion between charged lipid membranes.

A variety of ultrasound imaging techniques may be used to detect and quantify inflowing further contrast agent following the initial ultrasound irradiation, e.g. to generate a perfusion related image displaying a time-related measure of in-flowing contrast agent within the target region and thereby permitting discrimination between areas of different perfusion. The desired image may be obtained from analysis of individual scanlines or on a frame by frame basis; the former may be advantageous in areas with high rates of perfusion in order to obtain sufficient numbers of samples to discriminate areas with different perfusion, whereas the latter may be preferred in areas with low rates of perfusion.

Imaging modes which may be employed include B-mode and Doppler-based imaging, for example pulsed wave Doppler techniques such as power Doppler imaging. Non-linear imaging techniques based on effects such as higher harmonics (e.g. at 2, 3, 4 . . . times the imaging frequency), subharmonics (e.g. at ½, ⅓, ⅔, ¾ . . . of the imaging frequency), ultraharmonics (e.g. at 3/2, 5/4 . . . times the imaging frequency) and sum or difference frequencies (e.g. deriving from such harmonics and the imaging frequency), for example as described in U.S. Pat. No. 5410516, may if desired be used, as may techniques based on detection of sum or difference frequencies produced by two incident ultrasound signals of different frequencies, for example as described in published U.S. patent application Ser. No. 08/440,266, now U.S. Pat. No. 5,60/086. Second harmonic imaging may be particularly advantageous. Combinations of the above techniques, for example as in second harmonic power Doppler imaging may also be useful. In general, the images obtained may, for example, be displayed as colour maps representing rates of perfusion and may, if desired, be overlaid on conventional B-mode images of the target region.

The method of the invention may be tailored towards expected perfusion rates by appropriate selection of the energy level of the initial ultrasound pulse(s) (and thus the size of the investigated region containing destroyed or modified contrast agent) and the subsequent ultrasound imaging parameters, particularly the frame rate or time between individual pulses; where appropriate, ECG-triggering may be employed. If desired, the individual results may be spatially averaged, for example in per se known manner.

The method permits measurement of low perfusion rates which are below the detection limits of conventional Doppler techniques, and may also be used to estimate relative perfusion rates in the myocardium, where tissue movement renders conventional Doppler imaging ineffective. Imaging of the myocardium is advantageously performed a sufficient time after injection of the contrast agent for its peak concentration in the left ventricle to have passed, so that unwanted attenuation by contrast agent-containing left ventricular blood is minimised, and for wash-in rates of contrast agent into the myocardial tissue to have reached an approximately steady state. The essentially random flow patterns exhibited by blood and contrast agent at the capillary level ensure that the method of the invention, when used to measure at this level, avoids potentially anomalous results which might arise were the predominant flow pattern to be substantially perpendicular to the scanning system and therefore relatively undetectable. The method also has the advantage that its results are substantially independent of backscatter from the myocardium itself; this is advantageous since the levels of such backscatter may vary considerably for different regions of the myocardium as a result of differences in the echogenicity of such regions and in the attenuative properties of tissue, fluid etc. adjacent thereto lying between such regions and the ultrasound transducer. Furthermore, results obtained by the method are independent of the dose of contrast agent administered, provided that this is sufficient to allow the initial ultrasound irradiation to cause discernible modification or destruction of the echogenic effects of the contrast agent.

The following non-limitative Examples serve to illustrate the invention.

BRIEF DESCRIPTION OF DRAWINGS

In the accompanying drawings.

EXAMPLE 1

Figure 1:
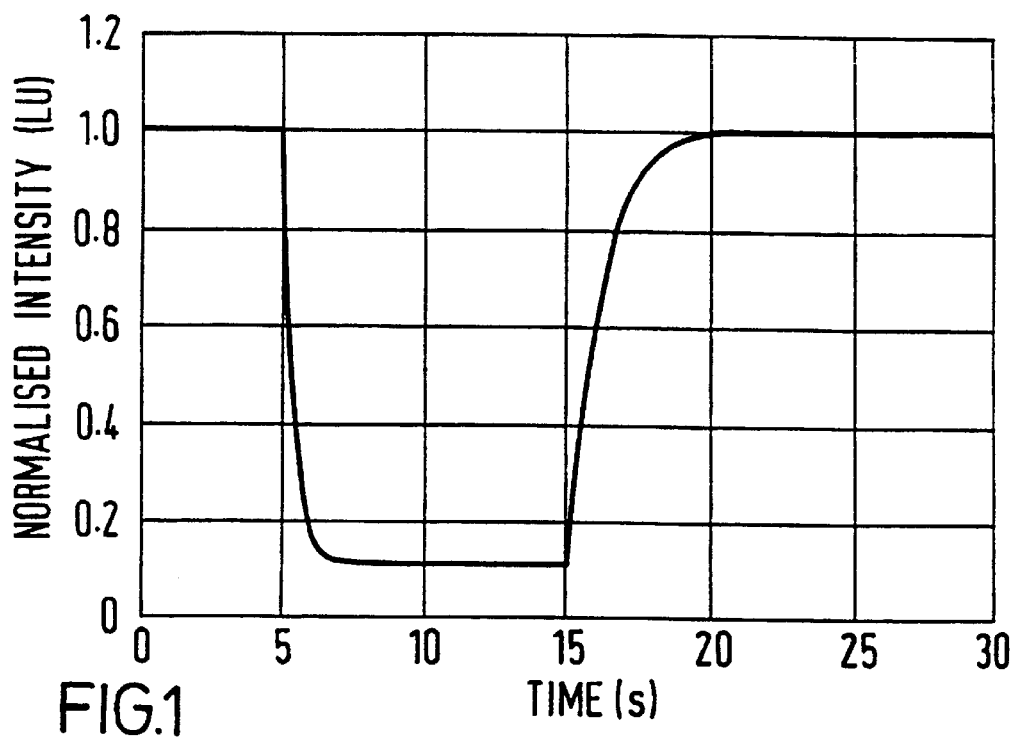
FIGS. 1–3 are normalised time-intensity curves obtained in accordance with the procedures of Examples 1–3 respectively. The intensity is represented in linear units (LU).

An anaesthetised dog is given an intravenous injection comprising 2 ml of an aqueous suspension of a gas-containing microparticulate contrast agent as described in WO-A-9317718. One minute after injection the heart is scanned for approximately 10 seconds using a Vingmed Sound System 5 scanner transmitting at 3.7 MHz and high acoustic power, thereby destroying all contrast agent in the imaged slice. The output power is then rapidly reduced by 12 dB with a compensating gain increase of 12 dB being made, and subsequent B-mode frames for several heartbeats are scan-converted and digitally stored. A plot of normalised signal intensity on a linear scale against time is prepared as shown in FIG. 1, each time point representing the average for a 5×5 pixel region. This plot shows the high power ultrasound irradiation starting at 5 seconds; the wash-in curve begins at 15 seconds when the output power is reduced, and shows a time to half peak (the "half-time") of about 0.7 seconds, indicating that the imaged region is normally perfused. A half-time image is generated by fitting the wash-in half-times to a monoexponential curve; this image, representing a perfusion image, is pseudocoloured and overlaid on the B-mode image. The perfusion image displays normal perfusion for all regions of the myocardium.

EXAMPLE 2

Figure 2:
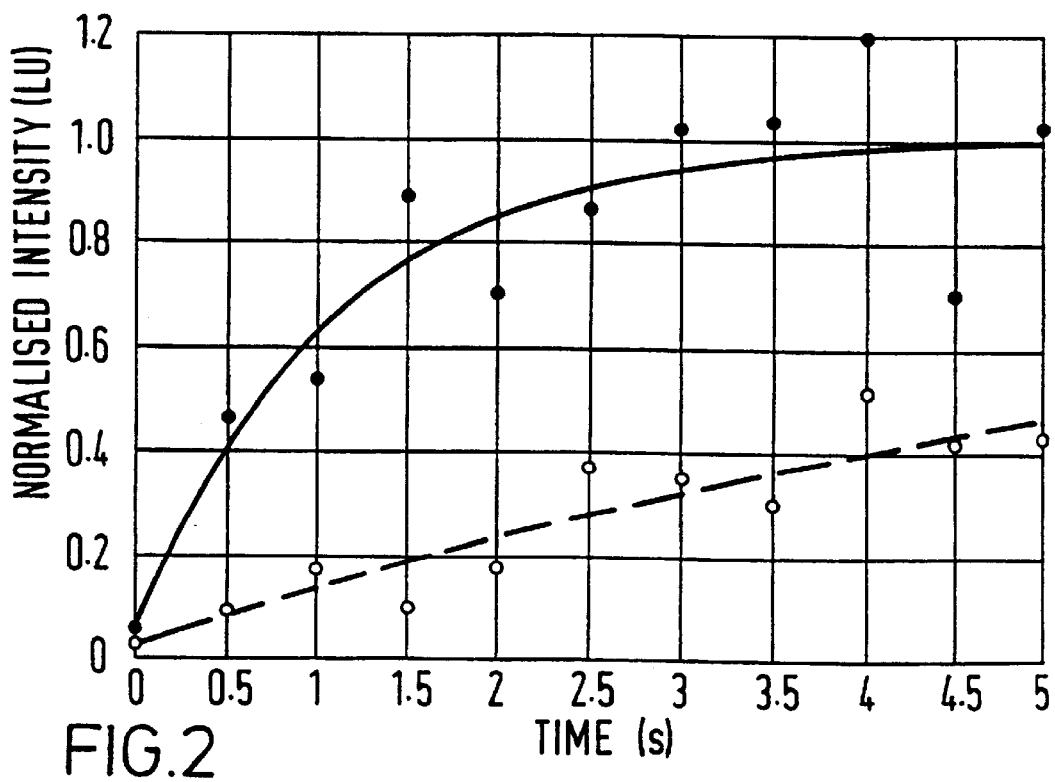

The left coronary artery of an anaesthetised dog was partially occluded to reduce the coronary blood flow to one region of the myocardium, thereby simulating the effect of a coronary artery stenosis. The dog was then given an intravenous injection comprising 2 ml of an aqueous suspension of a gas-containing microparticulate contrast agent as described in WO-A-9317718. One minute after injection the heart was scanned for approximately 10 seconds using a HDI 3000 scanner with a PS-3 transducer transmitting at 2.7 MHz and medium acoustic power, thereby destroying a significant fraction of the contrast agent in the imaged slice. The scanner was then rapidly set into ECG-triggered mode, receiving at 45.4 MHZ (i.e. the second harmonic), and end-systolic frames for several heartbeats were digitally stored. Minimal contrast agent destruction occurred during operation in ECG-triggered mode as a result of the reduced overall ultrasound exposure, so that wash-in curves representing inflow of fresh contrast agent were readily derived from the second harmonic signal intensities. FIG. 2 shows resulting plots of normalised signal intensities on a linear scale against time, each point representing the average of a 5×5 pixel region. The open circles show the results from a low perfusion region, whereas the closed circles are taken from a normally perfused region. Zero on the time axis corresponds to the point at which ECG-triggering commences. The drawn lines show the least mean square fit to these two data sets. The full line represents a curve in respect of a normally perfused region and shows a time to half peak of about 0.7 seconds. The dashed line represents a curve in respect of a low-perfused region, with a time to half peak of about 6 seconds, i.e. about eight times as long as normal. A pseudo-coloured image representing the wash-in half-times may be prepared and overlaid on the B-mode image.

EXAMPLE 3

(a) Hydrogenated phosphatidylserine (100 mg) in a 2% solution of propylene glycol in purified water (20 ml) is heated to 80° C. for 5 minutes and the resulting dispersion is allowed to cool to room temperature overnight. 1 ml portions are transferred to 2 ml vials, the headspace above each portion is flushed with perfluorobutane gas, and the vials are shaken for 45 seconds using an Espe CapMix® mixer for dental materials, yielding milky white microbubble dispersions.

(b) A sample of the milky white dispersion prepared in part (a) above is washed three times by centrifugation and removal of the infranatant, whereafter an equal volume of 10% sucrose solution is added. The resulting dispersion is lyophilised and then redispersed in distilled water, yielding a milky white microbubble dispersion with a volume median diameter of 3.5 μm, measured using a Coulter Counter.

(c) Hydrogenated phosphatidylserine (100 mg) in purified water (20 ml) is heated to 80° C. for 5 minutes and the resulting dispersion is cooled to 0° C. overnight. 1 ml of the dispersion is transferred to a 2 ml vial, to which is added 200 μl of 2-methylbutane (b.p. 28° C.). The vial is then shaken for 45 seconds using a CapMix® to yield an emulsion of diffusible component which is stored at 0° C. when not in use.

An injection syringe containing an amount of the perfluorobutane gas dispersion prepared in part (b) above corresponding to 2 μl of gas content is prepared along with an injection syringe containing an amount of the 2-methylbutane emulsion prepared in part (c) above corresponding to 2 μl of gas content and the contents are injected simultaneously into a dog using via a Y-piece connector and a catheter inserted into an upper limb vein.

Figure 3:
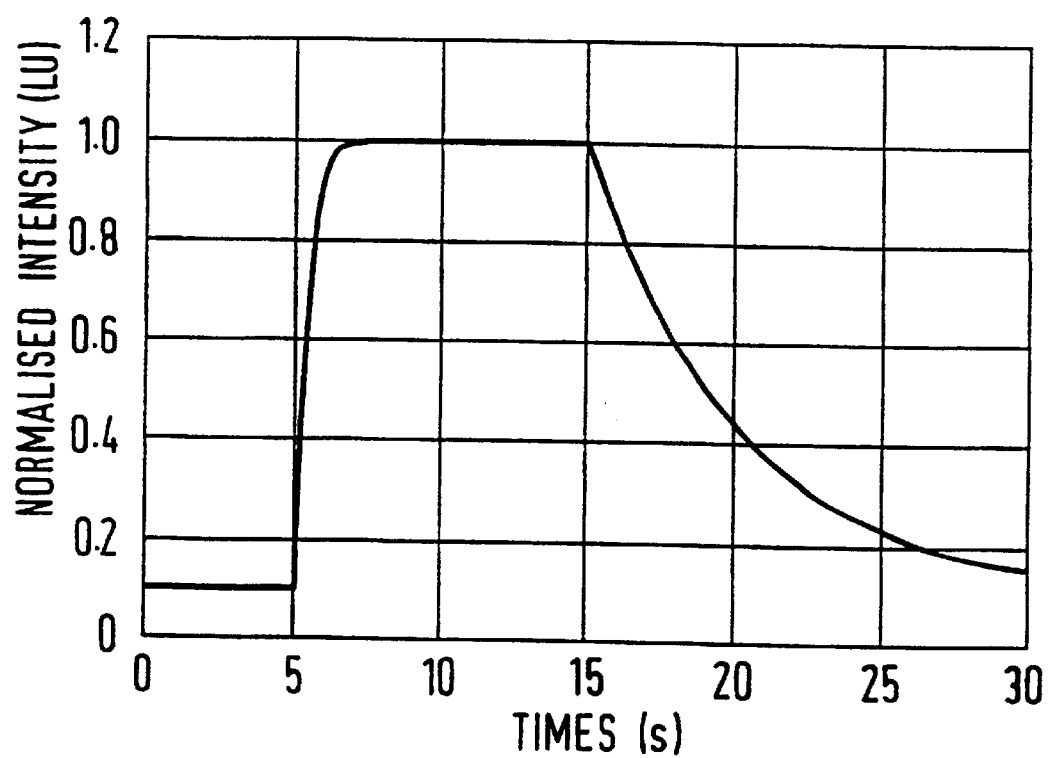

One minute after injection the heart is scanned for approximately 10 seconds using an ATL HDI 3000 scanner transmitting at 2.7 MHz and high acoustic power, and receiving at 5.4 MHz; this high energy ultrasound irradiation generates semi-stable free gas microbubbles, resulting in a significant enhancement of the intensity of backscatter from the myocardium. The output power is then rapidly reduced by 12 dB with a compensating gain increase of 12 dB being made, and subsequent second harmonic frames for several heartbeats are digitally stored. A plot of normalised signal intensity on a linear scale against time is prepared as shown in FIG. 3, each time point representing the average for a 5×5 pixel region. This plot shows the high power ultrasound irradiation starting at 5 seconds and generating a rapid rise in backscatter; the wash-out curve begins at 15 seconds when the output power is reduced, and shows a half-life of about 3.5 seconds, indicating that the imaged region is hypoperfused. A pseudo-coloured image of the wash-out half-time is prepared and overlaid on the second harmonic B-mode image; regions of low perfusion are easily identified and graded as poorly perfused.

What is claimed is:

1. A method of measuring tissue perfusion in a human or non-human animal subject which comprises administering to said subject an effective amount of an ultrasound contrast agent comprising a biocompatible gas stabilised by amphiphilic lipid material, irradiating tissue in a target region within said subject with at least one pulse of ultrasound having energy sufficient to destroy or discernibly modify the echogenic properties of a recognisable amount of the contrast agent in said target region, ultrasonically detecting signals in respect of the flow of either further contrast agent into said target region or modified contrast agent out of said target region, and plotting the normalised intensity of said detected signals on a linear scale against time to permit quantification of the rate of said flow.

2. A method as claimed in claim 1 wherein said biocompatible gas comprises a sulphur halide or a perfluorocarbon.

3. A method as claimed in claim 2 wherein said perfluorocarbon comprises a perfluorobutane.

4. A method as claimed in claim 1 wherein said amphiphilic lipid material comprises a membrane-forming lipid.

5. A method as claimed in claim 4 wherein said membrane-forming lipid comprises a phospholipid.

6. A method as claimed in claim 5 wherein at least 75% of said membrane-forming lipid comprises a negatively charged phospholipid.

7. A method as claimed in claim 6 wherein said negatively charged phospholipid comprises at least one phosphatidylserine.

8. A method as claimed in claim 1 wherein ultrasonic detection and quantification of the rate of flow of further contrast agent into the target region is effected using B-mode or Doppler-based imaging.

9. A method as claimed in claim 8 wherein non-linear imaging techniques are employed.

10. A method as claimed in claim 1 wherein the rate of flow of further contrast agent into the target region is displayed as a colour map.

11. A method as claimed in claim 10 wherein said colour map is overlaid on a conventional B-mode image of the target region.

* * * * *